United States Patent [19]

Lee et al.

[11] Patent Number: 5,500,222
[45] Date of Patent: Mar. 19, 1996

[54] TRANSDERMAL ADMINISTRATION OF OXYBUTYNIN

[75] Inventors: Eun S. Lee, Redwood City; Diane E. Nedberge; Su I. Yum, both of Los Altos, all of Calif.

[73] Assignee: Alza Corporation, Palo Alto, Calif.

[21] Appl. No.: 388,767

[22] Filed: Feb. 15, 1995

Related U.S. Application Data

[62] Division of Ser. No. 193,661, Feb. 8, 1994, Pat. No. 5,411,740, which is a continuation of Ser. No. 882,652, May 13, 1992, abandoned.

[51] Int. Cl.$^6$ ..................................................... A61F 13/02
[52] U.S. Cl. ........................... 424/448; 424/449; 514/946
[58] Field of Search ..................................... 424/449, 448; 514/946

[56] References Cited

U.S. PATENT DOCUMENTS

| | | | |
|---|---|---|---|
| 3,371,683 | 5/1971 | Zaffaroni | 128/268 |
| 3,598,122 | 8/1971 | Zaffaroni | 128/268 |
| 3,598,123 | 8/1971 | Zaffaroni | 128/268 |
| 3,797,494 | 3/1974 | Zaffaroni | 128/268 |
| 4,031,894 | 6/1977 | Urquhart et al. | 128/268 |
| 4,130,643 | 12/1978 | Smith | 424/238 |
| 4,130,667 | 12/1978 | Smith | 128/268 |
| 4,201,211 | 5/1980 | Chandrasekaran et al. | 128/260 |
| 4,286,592 | 9/1981 | Chandrasekaran | 128/260 |
| 4,299,826 | 11/1981 | Luedders | 424/181 |
| 4,314,557 | 2/1982 | Chandrasekaran | 128/260 |
| 4,335,115 | 6/1982 | Thompson et al. | 424/181 |
| 4,343,798 | 8/1982 | Fawzi | 424/240 |
| 4,379,454 | 4/1983 | Campbell et al. | 604/897 |
| 4,405,616 | 9/1983 | Rajadhyaksha | 424/244 |
| 4,435,180 | 3/1984 | Leeper | 604/896 |
| 4,474,845 | 10/1984 | Korol | 604/368 |
| 4,559,222 | 12/1985 | Enscore et al. | 424/28 |

(List continued on next page.)

FOREIGN PATENT DOCUMENTS

| | | |
|---|---|---|
| 902605 | 9/1985 | Belgium . |
| 0250125 | 6/1987 | European Pat. Off. . |
| 1001949 | 7/1962 | United Kingdom . |
| 9210231 | 6/1992 | WIPO . |
| WO9210231 | 6/1992 | WIPO . |
| WOA92/20377 | 11/1992 | WIPO . |

OTHER PUBLICATIONS

Keshary et al., "Development of Transdermal Delivery Systems for Oxybutynin In–Vivo bioavilability", Pharm. Res., (NY) 8 (10 Suppl) 1991, p. S205.
1992 Physicians Desk Reference, pp. 1332–1333.
Idson, "Percutaneous Absorpotion," J. Phar. Sci., vol. 64, No. 66, Jun. 1975, pp. 901–924.
Database WPIL Week 9219, Derwent Publications Ltd., London, G.B.; AN 92–157308 (19) & JP, A, 099 719 (Rido Chemical KK) 31 Mar. 1992.
Abstract of Japanese Patent No. JP 04273818–A, dated Feb. 28, 1991.
Abstract of Japanese Patent No. JP 04266821, dated Sep. 22, 1992.

*Primary Examiner*—Gabrielle Phelan
*Attorney, Agent, or Firm*—D. Byron Miller; Steven F. Stone; Edward L. Mandell

[57] ABSTRACT

The present invention is directed to the transdermal administration of oxybutynin together with a suitable permeation enhancer. The invention includes a transdermal drug delivery device comprising a matrix adapted to be placed in oxybutynin- and permeation enhancer-transmitting relation with the skin site. The matrix contains sufficient amounts of a permeation enhancer and of oxybutynin, in combination, to continuously administer to the skin for a predetermined period of time the oxybutynin to provide an effective therapeutic result. The invention is also directed to a method for the transdermal administration of a therapeutically effective amount of oxybutynin together with a skin permeation-enhancing amount of a suitable permeation enhancer.

6 Claims, 2 Drawing Sheets

U.S. PATENT DOCUMENTS

| | | | |
|---|---|---|---|
| 4,568,343 | 2/1986 | Leeper et al. | 604/896 |
| 4,573,995 | 3/1986 | Chen et al. | 604/896 |
| 4,588,580 | 5/1986 | Gale et al. | 424/21 |
| 4,645,502 | 2/1987 | Gale et al. | 604/896 |
| 4,704,282 | 11/1987 | Campbell et al. | 424/449 |
| 4,746,515 | 5/1988 | Cheng et al. | 424/449 |
| 4,784,857 | 11/1988 | Berry et al. | 424/449 |
| 4,788,062 | 11/1988 | Gale et al. | 424/449 |
| 4,816,258 | 3/1989 | Nedberge et al. | 424/448 |
| 4,820,720 | 4/1989 | Sanders et al. | 514/356 |
| 4,849,224 | 7/1989 | Chang | 424/449 |
| 4,849,226 | 7/1989 | Gale | 424/448 |
| 4,863,738 | 9/1989 | Taskovich | 424/449 |
| 4,865,848 | 9/1989 | Cheng et al. | 424/449 |
| 4,908,027 | 3/1990 | Enscore et al. | 604/890.1 |
| 4,928,680 | 5/1990 | Sandbank | 128/155 |
| 4,940,586 | 7/1990 | Baker et al. | 424/464 |
| 4,943,435 | 7/1990 | Baker et al. | 424/448 |
| 4,994,278 | 2/1991 | Sablotsky | 424/449 |
| 5,004,610 | 2/1991 | Osborne et al. | 424/448 |
| 5,071,656 | 12/1991 | Lee | 429/449 |

TRANSDERMAL ADMINISTRATION OF OXYBUTYNIN

This application is a division of application Ser. No. 08/193,661, filed Feb. 8, 1994, now U.S. Pat. No. 5,411,740 which is a continuation of Ser. No. 07/882,652, filed May 13, 1992, now abandoned and benefit of the filing date of said earlier filed application is claimed under 35 U.S.C. § 120.

FIELD OF THE INVENTION

This invention relates the efficacious and safe, controlled transdermal administration of oxybutynin and related compounds for the treatment of neurogenic bladder disorders.

BACKGROUND OF THE INVENTION

Neurogenic bladder disease is a disorder involving loss of control of urination. The major symptoms of this disease are urinary frequency, urinary retention or incontinence. There are two types of lesions that cause a neurogenic bladder. The first, upper motoneuron lesion, leads to hypertonia and hyperreflexia of the bladder, a spastic condition, giving rise to symptoms of urinary frequency and incontinence. The second lesion, a lower motoneuron lesion, involves hypotonia and hyporeflexia of the bladder. The major symptoms in this condition are urinary retention, since the voiding reflex has been lost, and incontinence, which occurs when the bladder "leaks", being full to overflowing.

The majority of neurogenic bladder patients have the spastic or hypertonic bladder. The clinician usually attempts to convert the condition of hyperreflexia and hypertonia to hypotonia, thereby treating the primary problem of incontinence. When the condition has been converted to hypotonia, it can be managed by intermittent catheterization. However, there is a significant population of patients who cannot be converted completely from the hypertonic to the hypotonic condition, and who still find they have to urinate every hour or are incontinent. For these patients, treatment with an anticholinergic drug is necessary. The drug of choice is oxybutynin (4-diethylamino-2-butynylphenylcyclohexylglycolate).

The use of oxybutynin chloride, as approved by the FDA in the United States, is described in the 1992 Physician's Desk Reference, pages 1332 through 1333 with reference to the drug Ditropan® manufacturea by Marion Merrell Dow. Oxybutynin is normally administered to human Deings orally at relatively high doses (5 mg tablets taken two to four times a day). Oxybutynin has been incorporated into tablets, capsules, granules or pills containing 1–5 mg, preferably 5 mg, of oxybutynin chloride, syrups containing 1–5 mg, preferably 5 mg, of oxybutynin chloride per 5 ml and transdermal compositions (creams or ointments) containing 1–10 weight percent ("wt %") oxybutynin chloride. See, BE 902605.

In U.S. Pat. No. 4,747,845, oxybutynin was listed as an agent that could be incorporated into a transdermal synthetic resin matrix system for extended duration drug release, but oxybutynin was not used in the device. In U.S. Pat. No. 4,928,680 oxybutynin was given as a pharmacologically active agent suitable for transdermal delivery, but as with the above reference, oxybutynin was not incorporated into the device.

Oxybutynin has been incorporated into a device having a water impermeable barrier layer, a reservoir containing oxybutynin in contact with the inner surface of the barrier layer and a removable protector layer in contact with the other surface of the reservoir. The reservoir is a polyurethane fiber mat impregnated with an aqueous solution containing 25 mg/ml of oxybutynin. The device was placed on a 20 μm thick polybutadiene film. The non-device carrying surface was in contact with 0.05 M isotonic phosphate buffer solution. The in vitro release rate measured was approximately 12 mg over 24 hours through a 49 cm$^2$ area or 10 μg/cm$^2$/hr. (U.S. Pat. No. 4,784,857 and EP 0 250 125).

In Pharm Res, "Development of Transdermal Delivery Systems of Oxybutynin: In-Vivo Bioavailability", P. Keshary et al., (NY)8 (10 Supp) 1991, p. S205 three types of transdermal delivery systems, using matrix-diffusion controlled and membrane-permeation controlled technologies were discussed. The in vitro permeation rate of about 9, 12 and 12 μg/cm$^2$/hr and in vitro release rates (sink condition) of about 1160, 402 and 57.2 μg/cm$^2$/hr were obtained from Silastic monolithic, acrylic pressure sensitive adhesive matrix and reservoir type delivery systems, respectively. In humans, steady state plasma concentrations of about 1.86 ng/ml were obtained after 6 hours of application of a single 20 cm$^2$ patch of the acrylic pressure sensitive adhesive matrix type.

The transdermal route of administration for drugs and other biologically active agents ("agents") has been proposed for a wide variety of systemically acting and locally acting agents on either a rate-controlled or non rate-controlled basis and is described in numerous technical publications and patents, such as U.S. Pat. Nos. 3,598,122; 3,598,123; 3,731,683; 3,797,494; 4,031,894; 4,201,211; 4,286,592; 4,314,557; 4,379,454; 4,435,180; 4,588,580; 4,645,502; 4,704,282; 4,788,062; 4,816,258; 4,908,027; 4,943,435; and 5,004,610. The disclosures of the above patents are incorporated herein by reference.

Just as certain drugs can irritate, sensitize or be otherwise toxic, so can permeation enhancers. The use of permeation enhancers for transdermal administration is described in numerous technical publications and patents, such as U.S. Pat. Nos. 4,940,586; 4,863,738; 4,820,720; 4,746,515; 4,568,343; 4,405,616; 4,379,454; 4,343,798; 4,335,115; 4,299,826; 4,130,667; 4,130,643; 4,046,886; British Patent No. 1,001,949 and Idson, Percutaneous Absorption, J. Phar. Sci., Vol. 64, No. 66, June 1975, pp. 901–924.

Permeation enhancers that are not normally toxic at the concentrations employed in cosmetic or medical compositions may exhibit toxic effects at the higher concentrations required to produce adequate permeation enhancement. No "universal" permeation enhancer has been identified. Instead, the behavior of permeation enhancers is highly idiosyncratic; a permeation enhancer effective for one drug may not be effective with other drugs, including closely related drugs.

Often, a permeation enhancer will exacerbate irritation and sensitization problems by allowing high transdermal permeation rates of the drug or permeation enhancer or permitting otherwise impermeable components of the transdermal device to enter the skin. Many potential permeation enhancers interact adversely with other components of transdermal devices. One major problem is that many potential permeation enhancers are not compatible with medically acceptable contact adhesives. Enhancers may improve the transdermal permeation rate adequately, but not adequately reduce the lag time.

The use of a permeation enhancer in any transdermal drug delivery device necessarily complicates the design and development of the device. Permeation enhancers cause compatibility problems throughout the delivery system. Instead of having to characterize the properties of the reservoir compositions, adhesives, and release-controlling materials with respect to just the drug, these materials must now have the proper characteristics with respect to both the drug and the permeation enhancer. Typically, drugs and permeation enhancers have very different physical and chemical properties, and, in most cases, the properties of mixtures of the drug with the permeation enhancer are unknown. For example, permeation enhancers can cause, among other problems, cohesive failure of adhesives and can partition through other components in the system.

As used herein, the term "oxybutynin" is used to designate oxybutynin, acid addition salts of oxybutynin and the related compounds thereof. The preferred active agent according to the present invention is oxybutynin itself. Oxybutynin is a base capable of forming acid addition salts with organic and mineral acids, for example, with hydrochloric acid to form oxybutynin chloride. Preferably, the device of this invention contains oxybutynin as the free base.

As used herein, the term "transdermal" delivery or application refers to the delivery or application of oxybutynin by passage through skin, mucosa and/or other body surfaces by topical application.

As used herein, the term "therapeutically effective" amount or rate refers to the amount or rate of oxybutynin needed to effect the desired therapeutic result.

As used herein, the term "monoesters" refers to those monoesters having from 10 to 20 carbon atoms.

As used herein, the term "glycerol monooleate" refers to glycerol monooleate itself or a mixture of monoglycerides wherein glycerol monooleate is present in the greatest amount.

As used herein, the term "glycerol monolaurate" refers to glycerol monolaurate itself or a mixture of monoglycerides wherein glycerol monolaurate is present in the greatest amount.

As used herein, the term "glycerol monolinoleate" refers to glycerol monolinoleate itself or a mixture of monoglycerides wherein glycerol monolinoleate is present in the greatest amount.

The above summarizes the primary characteristics recognized to date that affect suitability of oxybutynin and a permeation enhancer for transdermal administration. There are undoubtedly others, some of which have not yet been recognized. In order for oxybutynin and a permeation enhancer to be suitable for transdermal administration they must possess the right combination of all of these characteristics, a combination which is quite rare and unpredictable.

SUMMARY OF THE INVENTION

According to the present invention, it has been discovered that oxybutynin may be safely and efficaciously administered transdermally, together with a suitable permeation enhancer, preferably a monoglyceride or mixture of monoglycerides of fatty acids with a total monoester content of at least 51%. The invention includes a transdermal drug delivery device containing sufficient amounts of permeation enhancer and of oxybutynin, in combination, to provide systemic administration of oxybutynin through the skin for a predetermined period of time for the oxybutynin to provide an effective therapeutic result.

The invention is also directed to a method for the transdermal administration of a therapeutically effective amount of oxybutynin together with a skin permeation-enhancing amount of a suitable permeation enhancer.

DETAILED DESCRIPTION OF THE INVENTION AND PREFERRED EMBODIMENT

According to the present invention, it has been found that oxybutynin may be administered to the human body in a therapeutically effective amount via the transdermal route when it is co-administered with a suitable permeation enhancer. Therapeutic blood levels from about 0.5 ng/ml to about 3.0 ng/ml can be obtained from administration rates in the range of 0.08 mg/hr to 0.5 mg/hr. Representative skin permeation rates of oxybutynin through living human skin are in the range of about 12 $\mu g/cm^2/hr$ to about 40 $\mu g/cm^2/hr$, depending on the permeation enhancer. Therapeutic blood levels can be achieved within approximately 1–5 hours, and peak blood concentrations are achieved at about 3 hours when the system is worn for 24 hours. The range of desired and achievable system permeation rates of oxybutynin, arriving through the skin from a limited area, is 1–20 mg over a period of 24 hours. The system application is easily adapted for shorter or longer duration treatments, but generally 24 hours is the nominal duration for treatment.

Typical transdermal delivery devices are described in U.S. Pat. Nos. 3,598,122; 3,598,123; 4,286,592: 4,314,557; 4,379,454; 4,559,222; 4,573,995; and 4,849,225, for example. All of these are incorporated herein by reference. The co-administration of oxybutynin and a permeation enhancer as disclosed herein can be accomplished by using transdermal devices of these kinds.

Because of the wide variation in skin permeability from individual and from site to site on the same body, it may be preferable that oxybutynin and the permeation enhancer be administered from a rate-controlled transdermal delivery device. Rate control can be obtained either through a rate-controlling membrane or adhesive or through the other means disclosed in the patents noted above.

A certain amount of oxybutynin will bind to the skin, and it is accordingly preferred that the skin-contacting layer of the device include this amount of the agent as a loading dose.

Figure 1:
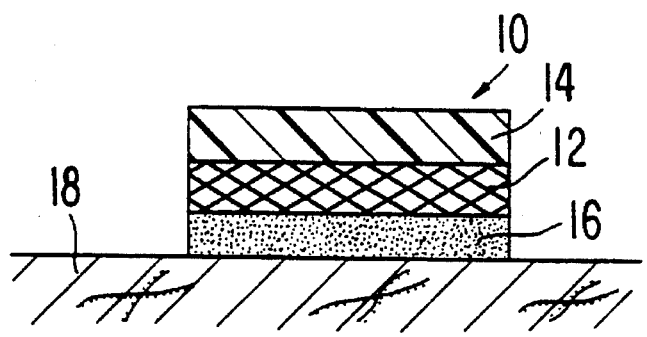
FIG. 1 is a cross-section through a schematic perspective view of one embodiment of transdermal therapeutic devices according to this invention.
Figure 2:
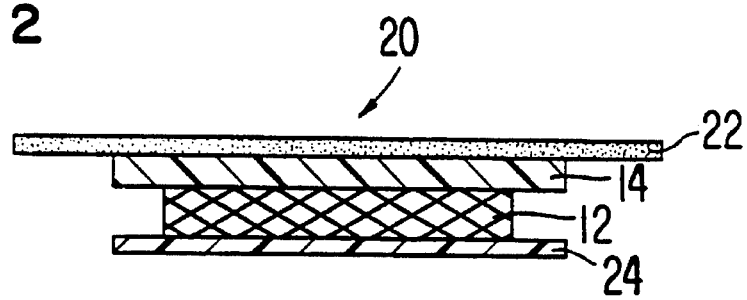
FIG. 2 is a cross-section through another embodiment of a transdermal therapeutic device according to this invention.
Figure 3:
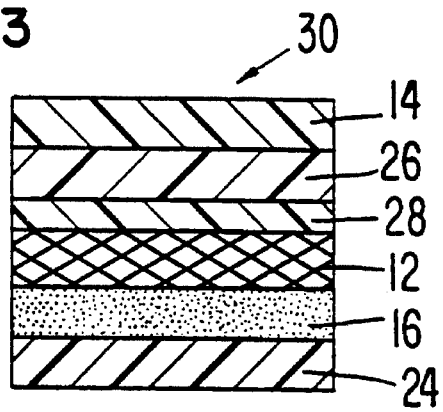
FIG. 3 is a cross-section through another embodiment of a transdermal therapeutic device according to this invention.

Examples of suitable transdermal delivery devices are illustrated in FIGS. 1, 2 and 3. In the drawings, the same reference numbers are used throughout the different figures to designate the same or similar components. The figures are not drawn to scale.

In FIG. 1, transdermal delivery device 10 comprises a reservoir 12 containing both oxybutynin and a suitable permeation enhancer. Reservoir 12 is preferably in the form of a matrix containing oxybutynin and enhancer dispersed therein. Reservoir 12 is sandwiched between a backing layer 14, which is permeable to water vapor, and an in-line contact adhesive layer 16. Preferably, the backing is a spun-laced polyester, such as Sontara®, a nylon reinforced polyurethane, such as NRU-100-C Flexcon® or a multilaminate film layer, such as EVA/EVA/polyvinyldienefluoride /EVA/ EVA film layer Saranex® Type 52. The device 10 adheres to the surface of the skin 18 by means of the adhesive layer 16. The adhesive layer 16 may optionally contain enhancer and/or oxybutynin. A strippable release liner (not shown in FIG. 1) is normally provided along the exposed surface of adhesive layer 16 and is removed prior to application of device 10 to the skin 18. Optionally, a rate-controlling membrane (not shown) may be present between the reservoir 12 and the adhesive layer 15.

Alternatively, as shown in FIG. 2, transdermal therapeutic device 20 may be attached to the skin or mucosa of a patient by means of an adhesive overlay 22. Device 20 is comprised of a oxybutynin- and permeation enhancer-containing reservoir 12 which is preferably in the form of a matrix containing oxybutynin and the enhancer dispersed therein. A backing layer 14, which is impermeable to oxybutynin, the permeation enhancer and water vapor, is provided adjacent one surface of reservoir 12. Adhesive overlay 22 maintains the device on the skin and may be fabricated together with, or provided separately from, the remaining elements of the device. With certain formulations, the adhesive overlay 22 may be preferable to the in-line contact adhesive 16 as shown in FIG. 1. This is true, for example, where the oxybutynin/enhancer reservoir contains a material which adversely affects the adhesive properties of the in-line contact adhesive layer 16. Backing layer 14 is preferably slightly larger than reservoir 12, and in this manner prevents the materials in reservoir 12 from adversely interacting with the adhesive in overlay 22. Optionally, a rate-controlling membrane (not shown in FIG. 2) may be provided on the skin-proximal side of reservoir 12. A strippable release liner 24 is also provided with device 20 and is removed just prior to application of device 20 to the skin.

In FIG. 3, transdermal delivery device 30 comprises a oxybutynin and permeation enhancer containing reservoir ("oxybutynin reservoir") 12 substantially as described with respect to FIG. 1. Permeation enhancer reservoir ("enhancer reservoir") 26 comprises permeation enhancer dispersed throughout and is substantially free of any undissolved oxybutynin. Enhancer reservoir 26 is preferably made from substantially the same matrix as is used to form oxybutynin reservoir 12. A rate-controlling membrane 28 for controlling the release rate of the permeation enhancer from enhancer reservoir 26 to oxybutynin reservoir 12 is placed between the two reservoirs. A rate-controlling membrane (not shown in FIG. 3) for controlling the release rate of the enhancer from oxybutynin reservoir 12 to the skin may also optionally be utilizea and would be present between adhesive layer 15 and reservoir 12.

The rate-controlling membrane may be fabricated from permeable, semipermeable or microporous materials which are known in the art to control the rate of agents into and out of delivery devices and having a permeability to the permeation enhancer lower than that of oxybutynin reservoir 12. Suitable materials include, but are not limited to, polyethylene, polyvinyl acetate and ethylene vinyl acetate copolymers.

Superimposed over the permeation enhancer reservoir 26 of device 30 is a backing 14 that is permeable to water vapor. On the skin-proximal side of reservoir 12 are an adhesive layer 16 and a strippable liner 24 which would be removed prior to application of the device 30 to the skin.

In the embodiments of FIGS. 1, 2 and 3, the carrier or matrix material of the reservoirs has sufficient viscosity to maintain its shape without oozing or flowing. If, however, the matrix or carrier is a low viscosity flowable material such as a liquid or a gel, the composition can be fully enclosed in a pouch or pocket, as known to the art from U.S. Pat. No. 4,379,454 (noted above), for example, and as illustrated in FIG. 4.

Figure 4:
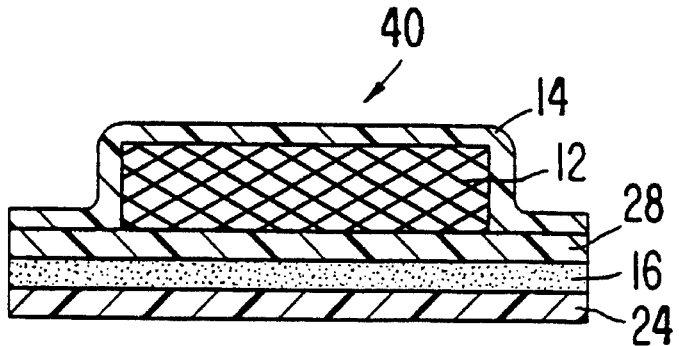
FIG. 4 is a cross-section through yet another embodiment of a transdermal therapeutic device according to this invention.

Device 40 shown in FIG. 4 comprises a backing member 14 which serves as a protective cover for the device, imparts structural support, and substantially keeps components in device 40 from escaping the device. Device 40 also includes reservoir 12 which contains the oxybutynin and permeation enhancer and bears on its surface distant from backing member 14 a rate-controlling membrane 28 for controlling the release of oxybutynin and/or permeation enhancer from device 40. The outer edges of backing member 14 overlay the edges of reservoir 12 and are joined along the perimeter with the outer edges of the rate-controlling membrane 28 in a fluid-tight arrangement. This sealed reservoir may be effected by pressure, fusion, adhesion, an adhesive applied to the edges, or other methods known in the art. In this manner, reservoir 12 is contained wholly between backing member 14 and rate-controlling membrane 28. On the skin-proximal side of rate-controlling membrane 22 are an adhesive layer 16 and a strippable liner 24 which would be removed prior to application of the device 40 to the skin.

In an alternative embodiment of device 40 of FIG. 4, reservoir 12 contains the permeation enhancer only and is substantially free of oxybutynin. The oxybutynin and an additional amount of permeation enhancer are present in adhesive layer 16 which acts as a separate reservoir.

The oxybutynin and the permeation enhancer can be co-extensively administered to human skin or mucosa by direct application to the skin or mucosa in the form of an ointment, gel, cream or lotion, for example, but are preferably administered from a skin patch or other known transdermal delivery device which contains a saturated or unsaturated formulation of oxybutynin and the enhancer.

The formulation may be aqueous or non-aqueous based. The formulation should be designed to deliver the oxybutynin and the permeation enhancer at the necessary release rates. Aqueous formulations typically comprise water or water/ethanol and about 1–2 wt % of a gelling agent, an example being a hydrophilic polymer such as hydroxyethylcellulose or hydroxypropylcellulose. Typical non-aqueous gels are comprised of silicone fluid or mineral oil. Mineral oil-based gels also typically contain 1–2 wt % of a gelling agent such as colloidal silicon dioxide. The suitability of a particular gel depends upon the compatibility of its constituents with both the oxybutynin and the permeation enhancer and any other components in the formulation.

The reservoir matrix should be compatible with oxybutynin, the permeation enhancer and any carrier therefor. The term "matrix" as used herein refers to a well-mixed composite of ingredients fixed into shape. When using an aqueous-based formulation, the reservoir matrix is preferably a hydrophilic polymer, e.g., a hydrogel. When using a non-aqueous-based formulation, the reservoir matrix is preferably composed of a hydrophobic polymer. Suitable polymeric matrices are well known in the transdermal drug delivery art, and examples are listed in the above-named patents previously incorporated herein by reference.

A typical laminated system would comprise a polymeric membrane and/or matrix such as ethylene vinyl acetate (EVA) copolymers, such as those described in U.S. Pat. No.

4,144,317, preferably having a vinyl acetate (VA) content in the range of from about 9% up to about 60% and more preferably about 28% to about 60% VA. Polyisobutylene/oil polymers containing from 4–25% high molecular weight polyisobutylene and 20–81% low molecular weight polyisobutylene with the balance being an oil such as mineral oil or polybutynes may also be used as the matrix material.

The aforementioned patents describe a wide variety of materials which can be used for fabricating the various layers or components of the transdermal oxybutynin delivery devices according to this invention. This invention therefore contemplates the use of materials other than those specifically disclosed herein, including those which may hereafter become known to the art to be capable of performing the necessary functions.

The amount of oxybutynin present in the therapeutic device and required to achieve an effective therapeutic result depends on many factors, such as the minimum necessary dosage of oxybutynin for the particular indication being treated; the solubility and permeability of the matrix, of the adhesive layer and of the rate-controlling membrane, if present; and the period of time for which the device will be fixed to the skin. The minimum amount of oxybutynin is determined by the requirement that sufficient quantities of oxybutynin must be present in the device to maintain the desired rate of release over the given period of application. The maximum amount for safety purposes is determined by the requirement that the quantity of oxybutynin present cannot exceed a rate of release that reaches toxic levels. The oral lethal dose discovered for rats is 1220 mg/kg.

When a constant oxybutynin delivery rate is desired, the oxybutynin is normally present in the matrix or carrier at a concentration in excess of saturation, the amount of excess being a function of the desired length of the oxybutynin delivery period of the system. The oxybutynin may, however, be present at a level below saturation without departing from this invention as long as oxybutynin is continuously administered to the same skin or mucosa site in an amount and for a period of time sufficient to provide the desired therapeutic rate and delivery profile of oxybutynin delivery.

The permeation enhancer is dispersed through the matrix or carrier, preferably at a concentration sufficient to provide permeation-enhancing amounts of enhancer in the reservoir throughout the anticipated administration period. Where there is an additional, separate permeation enhancer matrix layer as well, as in FIGS. 3 and 4, the permeation enhancer normally is present in the separate reservoir in excess of saturation.

The preferred permeation enhancers of the present invention are a monoglyceride or a mixture of monoglycerides of fatty acids with a total monoester content of at least 51%. Fatty acids may be saturated or unsaturated and straight or chained, and include, for example, lauric acid, myristic acid, stearic acid, oleic acid, linoleic acid and palmitic acid. Monoglycerides are generally available as a mixture of monoglycerides, with the mixture deriving its name from the monoglyceride present in the greatest amount. Monoglyceride permeation enhancers include, for example, glycerol monooleate, glycerol monolaurate and glycerol monolinoleate. In a more preferred embodiment, the permeation enhancer is glycerol monooleate.

In addition to oxybutynin and a suitable permeation enhancer, which are essential to the invention, the matrix or carrier may also contain dyes, pigments, inert fillers, excipients and other conventional components of pharmaceutical products or transdermal so devices known to the art.

In the present invention, oxybutynin is delivered at a therapeutically effective rate (that is, a rate that provides a desired therapeutic effect) and the permeation enhancer is delivered at a permeation-enhancing rate (that is, a rate that provides increased permeability of the application site to the oxybutynin) for a predetermined time period and in the required delivery pattern.

A preferred embodiment of the present invention comprises a method of treating any disorder in which it is therapeutic to administer a therapeutically effective amount of one or more of the compounds of the present invention to a patient suffering from such disorder.

Another preferred embodiment of the present invention comprises a method of treating neurogenic bladder disorders, e.g., urinary frequency or incontinence. To be useful in treating a neurogenic bladder disorder. oxybutynin should be present in plasma at levels above about 0.5 ng/ml, preferably at levels above about 1.0 ng/ml and most preferably at levels of about 2.0 ng/ml. To achieve this result, oxybutynin is delivered at a therapeutic rate of at least about 40–200 μg per hour, but typically of at least 80 μg/hr, and more typically at about 80–160 μg/hr, for the treatment period, usually about 24 hours to 7 days.

The administration rate through the skin should be sufficient to minimize the size of the device. The size of the device of this invention can vary from less than 1 $cm^2$ to greater than 200 $cm^2$. A typical device, however, will have a size within the range of 5–50 $cm^2$. The delivery device containing the oxybutynin and a permeation enhancer is placed on a user such that the device is delivering oxybutynin in a therapeutically effective amount to the user to treat a neurogenic bladder disorder.

The length of time of oxybutynin presence and the total amount of oxybutynin in the plasma can be changed following the teachings of this invention to provide different treatment regimens. Thus, they can be controlled by the amount of time during which exogenous oxybutynin is delivered transdermally to an individual or animal.

The devices of this invention can be designed to effectively deliver oxybutynin for an extended time period of from several hours up to 7 days or longer. Seven days is generally the maximum time limit for application of a single device because the adverse affect of occlusion of a skin site increases with time and the normal cycle of sloughing and replacement of the skin cells occurs in about 7 days. The transdermal therapeutic devices of the present invention are prepared in a manner known in the art, such as by those procedures, for example, described in the transdermal device patents listed previously herein. Having thus generally described the invention, the following specific examples describe preferred embodiments thereof.

DETAILED DESCRIPTION OF EXAMPLES

The devices for Example 1 were prepared as follows:

A. Formulation without a Permeation Enhancer

A formulation containing 30 wt % oxybutynin base in a matrix of EVA 40 (U.S.I. Chemicals, Ill.) was prepared by dissolving the oxybutynin base and EVA 40 in methylene chloride. The solution was poured onto a sheet of fluorocarbon diacrylate ("FCD")/polyester release liner to dry. The dried material was pressed to 5 mil (a. 0.1 mm) thickness between two sheets of FCD/polyester release liner at 75° C. The resulting film was laminated to a flexible cloth backing (spun laced polyester, 1.3 oz/$yd^2$), and 2.0 $cm^2$ discs were cut from the laminate.

B. Formulations with Permeation Enhancers

Formulations containing oxybutynin base at 30 wt %, and various permeation enhancers glycerol monolaurate, glycerol monooleate, and glycerol monolinoleate) at 25 wt % in a matrix of EVA 40 were prepared by dissolving the oxybutynin base, permeation enhancer and EVA 40 in methylene chloride. The same procedure as described above was then used to make the device.

The glycerol monooleate (GMO) used was Myverol® 18–99K glycerol monooleate (Eastman Kodak Chemicals), which has a glycerol monooleate content of 61% and a total monoester content of 93%, the glycerol monolinoleate (GMLO) used was Myverol® 18–92K glycerol monolinoleate, which has a glycerol monolinoleate content of 68% and a minimum total monoester content of 90%, and the glycerol monolaurate (GML) used was Grindtek® ML 90 glycerol monolaurate, which has a glycerol monolaurate content of 90% and a minimum total monoester content of 90%.

C. Device with In-line Adhesive

Each of the oxybutynin matrix/cloth backing laminates were divided in half, and one half of each was laminated to 3M acylate transfer adhesive MSP 32589 (1.6 mil, an acrylate adhesive with 2–5% acid functionality). Before testing, each final laminate was equilibrated for at least 5 days to allow the enhancer and oxybutynin to partition into the contact adhesive. The edges of the devices with in-line adhesive were masked with polyester tape so that the oxybutynin reservoir edges were not exposed to the epidermis or solutions when they were tested.

The devices for Examples 2, 4 and 5 are prepared as follows:

A. Formulation containing GMO

A formulation containing 27 wt % oxybutynin base and 27 wt % GMO (Myverol® 18–99K glycerol monooleate) in a matrix of EVA 40 was prepared using a Brabender Mixer and a 50 cc mixing bowl. The EVA 40 was added to the mixing bowl and mixed until pellets were no longer visible. The oxybutynin base was slowly added to the mixing bowl. Mixing was continued for an additional 10 minutes after addition was complete. GMO was heated to 40° C. and added very slowly to the mixing bowl. Addition time was approximately 45 minutes. The bowl was then closed and mixing continued for at least 20 minutes before removing the completed oxybutynin mix from the bowl.

The oxybutynin mix was calendared to 5 mil thickness between release liners (FCD/polyester). Five one-foot sections of the oxybutynin film were heat laminated to Medpar® backing (medium density polyethylene layer/aluminum polyester layer/EVA layer). Three of the oxybutynin film/backing laminates were laminated to 3M acrylate transfer adhesive MSP 1006 P.

EXAMPLE 1

The in vitro transdermal oxybutynin permeation rates through the epidermis of two human skin donors from devices described above were determined. For each device tested, the release liner was removed and the oxybutynin-releasing surface was placed against the stratum corneum side of a disc of human epidermis which had been blotted dry just prior to use. The excess epidermis was wrapped around the device so that none of the device edge was exposed to the receptor solution. The device covered with epidermis was attached to the flat side of the Teflon® holder of a release rate rod using nylon mesh and metal string. The rods were reciprocated in a fixed volume of receptor solution 0.05 M phosphate buffer, pH 6.5. The entire receptor solution was changed at each sampling time. The temperature of the receptor solution in the water bath was maintained at 35° C.

Results are summarized in the following table:

TABLE 1

|  | Permeation Enhancer | Average Transdermal Oxybutynin (Base) Permeation Rate $\mu g/cm^2/hr$ for 0–96 hrs |
|---|---|---|
| With adhesive | None (control) | 1.21 |
|  | GML | 3.74 |
|  | Myverol ® 18-99K | 3.09 |
|  | Myverol ® 18-92K | 2.40 |
| Without adhesive | None Control | 1.13 |
|  | GML | 4.24 |
|  | Myverol ® 18-99K | 3.59 |
|  | Myverol ® 18-92K | 2.47 |

EXAMPLE 2

The in vitro transdermal oxybutynin permeation rates through the epidermis of five human skin donors from devices described above were determined as described in Example 1. The control formulation contained 30 wt % oxvbutynin base (no permeation enhancer) in an EVA 40 matrix. No in-line adhesive was present. The other formulation contained 28 wt % oxybutynin base and 28 wt % Myverol® 18–99K glycerol monooleate in an EVA 40 matrix. There was a 3M acrylate in-line adhesive present. This same device was used in the in vivo testing described in Examples 3 and 4. The results are summarized in the following table:

TABLE 2

| Skin Donor | Control Without Permeation Enhancer $\mu g/cm^2/hr$ | With Permeation Enhancer $\mu g/cm^2/hr$ |
|---|---|---|
| 1 | 4.7 | 15.4 |
| 2 | 3.1 | 6.8 |
| 3 | 2.6 | 9.4 |
| 4 | 2.5 | 4.7 |
| 5 | 2.6 | 5.4 |

EXAMPLE 3

This experiment was carried out using standard glass diffusion cells which consist of a donor compartment with a 4 ml capacity, and a receptor compartment with a 22 ml capacity. A circular piece of epidermis was placed in each diffusion cell (permeation area=1.13 cm$^2$) in a horizontal position between a lower capped receptor compartment and an upper capped donor compartment. The receptor compartment has both a venting tube (uncapped) and a sampling port (capped). The stratum corneum side of the epidermis faced the donor compartment. An O-ring was positioned between the epidermis and the donor compartment, and a clamp held the compartments together. The receptor solution, 22 ml of 0.05 M phosphate buffer solution, pH 6.5, was added to each receptor compartment. The cells were placed in a temperature controlled water bath shaker at 35° C. and allowed to come to temperature before the donor solution was added.

A total of five donor solutions were tested, and the donor volume was 0.2 ml in each case. The donor solutions tested were oxybutynin saturated in 0.05 M phosphate buffer solution, pH 6.5, oxybutynin saturated in mineral oil, oxybutynin saturated in a solution of 30% ethanol in phosphate buffer, oxybutynin saturated in a solution of 10.6% Myverol 18–99K glycerol monooleate in mineral oil, and oxybutynin saturated in a solution of 10.6% glycerol monolaurate in mineral oil. All donor solutions were at pH 6.5.

At each time interval, the receptor solution was removed from the test cell and replaced with an equal volume of fresh receptor solution previously equilibrated at 35° C. The receptor solutions for each time interval were then assayed for oxybutynin, by HPLC (Zorbax Rx-C8, 15 cm×4.6 mm ID, 5 μm, 30% acetonitrile/water, 0.06% dimethyloctylamine, 0.03% $H_3PO_4$, 220 nm, 1.0 ml/min), to calculate the permeation rate of oxybutynin through epidermis from the donor solution.

Figure 5:
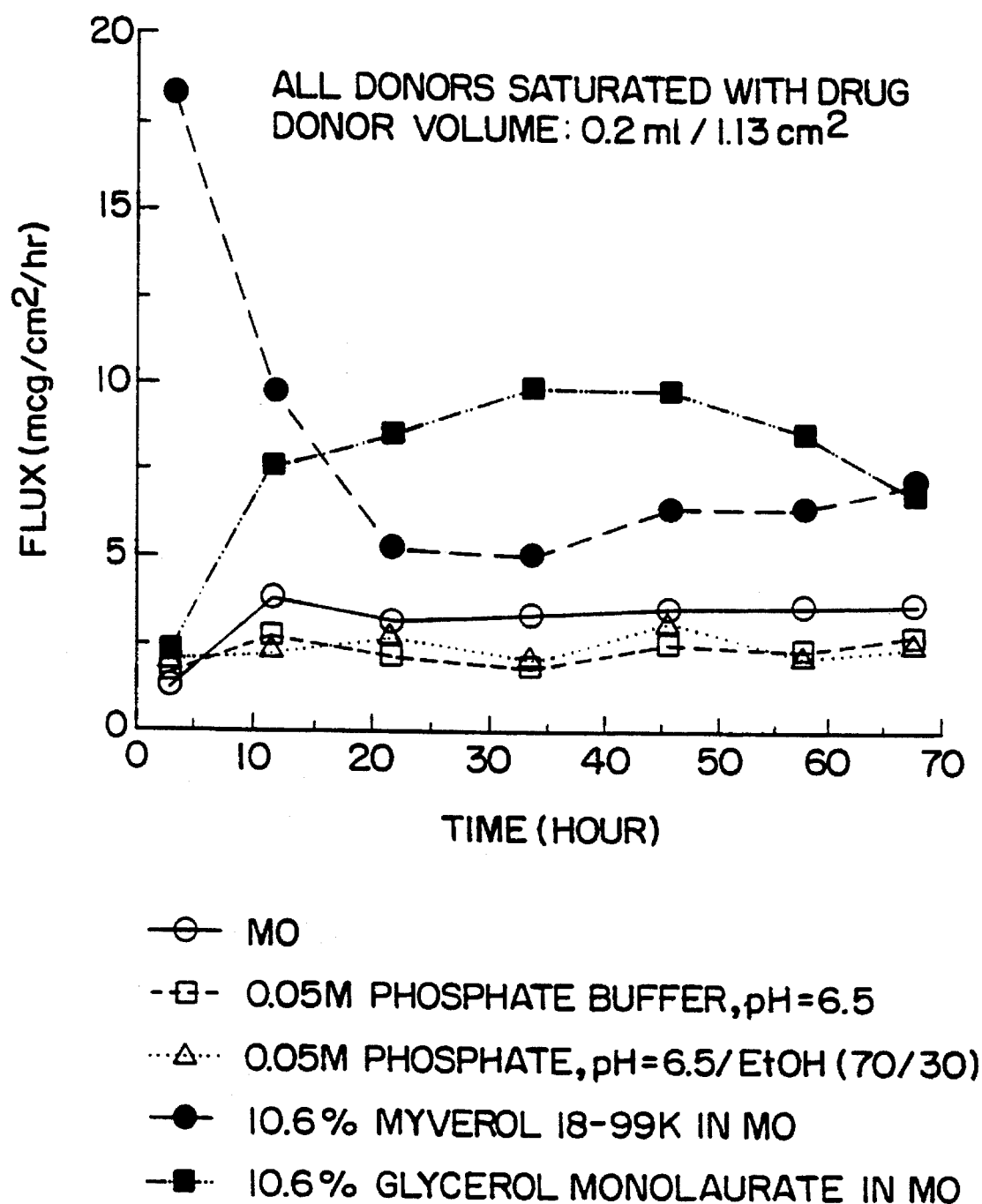
FIG. 5 shows the oxybutynin permeation rate through the epidermis at 35° C. with various permeation enhancers.

As can be seen in FIG. 5, glycerol monolaurate and glycerol monolinoleate increased the permeation rate of oxybutynin, whereas ethanol showed the same permeation rate as the donor solution containing no permeation enhancer.

EXAMPLE 4

The in vivo plasma levels of oxybutynin were measured for two body sites. A 10 cm² device was worn on the penis for 10½ hours and two 10 cm² devices were worn on the inner thigh for 24 hours. A control sample was drawn before applying the systems. The device worn on the penis produced a plasma oxybutynin level of 2.0 ng/mL within 4 hours, and the levels varied between 1.4 and 2.1 ng/mL during the following 6½ hours of wearing. The systems worn on the inner thigh produced a plasma oxybutynin concentration of 0.9 ng/mL after 12 hours of wearing, and after 24 hours of wearing the level had reached 1.1 ng/mL.

The in vivo plasma oxybutynin concentration were also measured in two additional subjects who each wore two 10 cm² systems on the inner thigh. One subject achieved a plasma oxybutynin concentration of 2.0 ng/mL after 9 hours, and the plasma level was 1.7 ng/mL after 24 hours of wearing. The other subject achieved a plasma level of 0.7 ng/mL after 12 hours, and the plasma level was 0.8 ng/mL after 24 hours.

EXAMPLE 5

The residual oxybutynin in devices which had been worn by subjects was measured and compared to the oxybutynin content of devices which had not been worn. The results are summarized in the following table:

TABLE 3

| Subject # | Site | Measured Drug Loss (mg/20 cm²/day) |
|---|---|---|
| 1 | inner thigh | 5.8 |

TABLE 3-continued

| Subject # | Site | Measured Drug Loss (mg/20 cm²/day) |
|---|---|---|
| 2 | inner thigh | 8.6 |
| 3 | chest | 6.7 |
| 4 | abdomen | 7.2 |
| 5 | penis | 19.2 |

Having thus generally described the present invention and described certain specific embodiments thereof including the embodiments that the applicants consider the best mode of practicing their invention, it will be readily apparent that various modifications to the invention may be made by workers skilled in the art without departing from the scope of this invention which is limited only by the following claims.

What is claimed is:

1. A method for the transdermal administration of oxybutynin at a therapeutically effective rate comprising the step of placing an oxybutynin transdermal delivery device onto an area of skin of a person, the oxybutynin transdermal delivery device comprising:

(a) an oxybutynin reservoir comprising oxybutynin base and a permeation enhancing amount of a monoglyceride or mixture of monoglycerides of fatty acids with a total monoesters content of at least 51%;

(b) a backing on or adjacent the skin-distal surface of the oxybutynin reservoir; and (c) means for maintaining the oxybutynin reservoir in oxybutynin- and permeation enhancer- transmitting relation with the skin; wherein oxybutynin is administered at a therapeutically effective rate and the monoglyceride or mixture of monoglycerides of fatty acids is simultaneously administered to the area of skin at a rate which is sufficient to substantially increase the permeability of the area to the oxybutynin.

2. A method for the transdermal administration of oxybutynin, which method comprises:

(a) administering oxybutynin base at a therapeutically effective rate to an area of skin; and (b) simultaneously administering a permeation enhancing amount of a monoglyceride or mixture of monoglycerides of fatty acids with a total monoesters content of at least 51% to the area of skin at a rate which is sufficient to substantially increase the permeability of the area to the oxybutynin.

3. A method according to claim 2 wherein the permeation enhancer is glycerol monooleate, glycerol monolaurate or glycerol monolinoleate.

4. A method according to claim 2 wherein the oxybutynin is administered through the skin at a rate of at least 0.08 mg/hour for a predetermined period of time.

5. A method according to claim 2 wherein the oxybutynin is administered through the skin at a permeation rate of at least 12 μg/cm²/hr for a predetermined period of time.

6. A method according to claim 2 wherein the backing is permeable to water vapor.

* * * * *